United States Patent [19]

Buerstinghaus et al.

[11] 4,424,215
[45] Jan. 3, 1984

[54] OXIMINOPHOSPHORIC ACID DERIVATIVES, AND THEIR USE FOR CONTROLLING PESTS

[75] Inventors: Rainer Buerstinghaus, Weinheim; Karl Kiehs, Lampertheim; Walter Seufert, Ludwigshafen; Heinrich Adolphi, Limburgerhof, all of Fed. Rep. of Germany

[73] Assignee: BASF Aktiengesellschaft, Fed. Rep. of Germany

[21] Appl. No.: 411,870

[22] Filed: Aug. 26, 1982

[30] Foreign Application Priority Data

Sep. 5, 1981 [DE] Fed. Rep. of Germany ....... 3135182

[51] Int. Cl.³ ...................... A01N 57/14; C07F 9/165
[52] U.S. Cl. ..................................... 424/210; 260/940
[58] Field of Search ........................ 260/940; 424/210

[56] References Cited

U.S. PATENT DOCUMENTS 2,957,016 10/1960 Diamond ............................. 260/944
3,911,055 10/1975 Lorenz et al. ....................... 260/940

*Primary Examiner*—Anton H. Sutto
*Attorney, Agent, or Firm*—Keil & Witherspoon

[57] ABSTRACT

Oximinophosphoric acid derivatives of the formula

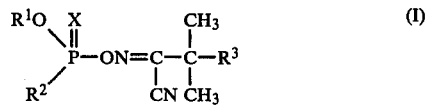

where $R^1$, $R^2$ and $R^3$ have the meanings given in the description, processes for their preparation, and their use for controlling pests.

5 Claims, No Drawings

OXIMINOPHOSPHORIC ACID DERIVATIVES, AND THEIR USE FOR CONTROLLING PESTS

The present invention relates to oximinophosphoric acid derivatives, processes for their preparation, pesticides which contain these compounds as active ingredients, and a process for controlling pests with these active ingredients.

Oximinophosphoric acid derivatives have been disclosed in, for example, German Published Application DAS No. 1,052,981 and German Laid-Open Application DOS No. 2,243,370, and are useful for controlling insects and arachnids.

We have found that oximinophosphoric acid derivatives of the formula

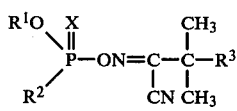
(I)

where $R^1$ is straight-chain or branched alkyl of not more than 4 carbon atoms, $R^2$ is a straight-chain or branched alkoxy or alkylthio group of not more than 4 carbon atoms, straight-chain or branched alkoxyalkylthio of not more than 6 carbon atoms, straight-chain or branched alkyl of not more than 3 carbon atoms, phenyl or a straight-chain or branched alkylamino or dialkylamino radical where each alkyl is of not more than 4 carbon atoms, $R^3$ is straight-chain or branched alkoxy of not more than 4 carbon atoms or methoxymethyl, and X is oxygen or sulfur, possess very high insecticidal, acaricidal and nematicidal activity, and are superior to conventional active ingredients having a similar structure or the same direction of action.

Straight-chain or branched alkyl radicals $R^1$ are, for example, methyl, ethyl, propyl, isopropyl, butyl and isobutyl, and straight-chain or branched alkyl, alkoxy, alkylthio and alkoxyalkylthio radicals $R^2$ are, for example, methyl, ethyl, n-propyl, isopropyl, methoxy, ethoxy, propoxy, butoxy, methylthio, ethylthio, n-propylthio, isopropylthio, n-butylthio, sec.-butylthio, isobutylthio, 2-methoxyethylthio, 2-ethoxyethylthio and 2-isopropoxyethylthio. Suitable alkylamino and dialkylamino radicals $R^2$ are, for example, methylamino, dimethylamino, ethylamino, diethylamino, methylethylamino, n-butylamino and di-n-butylamino.

Preferred substituents $R^1$ are methyl and ethyl, and preferred substituents $R^2$ are methoxy, ethoxy, 2-methoxyethylthio, 2-ethoxyethylthio, methyl, ethyl, phenyl, methylamino, dimethylamino and isopropylamino.

The oximinophosphoric acid derivatives of the formula I can be obtained by reacting an oxime of the formula III in the presence or absence of an acid acceptor, or reacting an alkali metal salt, alkaline earth metal salt or unsubstituted or substituted ammonium salt of this oxime, with a (thiono)(thiol)phosphoric(phosphonic) acid ester (amide) halide of the formula III, according to the following equation:

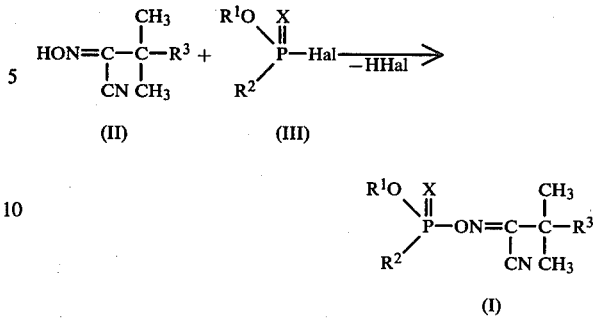

In these formulae, $R^1$, $R^2$ and $R^3$ have the above meanings and Hal is halogen, preferably chlorine.

The reaction is advantageously carried out in a solvent or diluent which is inert to the reactants. Examples of suitable solvents and diluents are aliphatic and aromatic hydrocarbons and aliphatic and aromatic chlorohydrocarbons, eg. petroleum ether, benzene, toluene, xylene, gasoline, dichloromethane, chloroform, tetrachloromethane, 1,2-dichloroethane and chlorobenzene, ethers, eg. diethyl ether, di-n-butyl ether, methyl tert-.butyl ether, tetrahydrofuran and dioxane, ketones, eg. acetone, methyl ethyl ketone and methyl isopropyl ketone, and nitriles, eg. acetonitrile and propionitrile, as well as mixtures of these.

Suitable acid acceptors are the bases conventionally used in the phosphorylation of hydroxy compounds. Alkali metal carbonates and alcoholates, eg. sodium carbonate, potassium carbonate, sodium methylate, potassium methylate, sodium ethylate and potassium ethylate, and aliphatic, aromatic and heterocyclic amines, eg. triethylamine, dimethylamine, piperidine, dimethylaniline, dimethylbenzylamine and pyridine, have proved particularly useful. In some cases it is advantageous to use an alkyl-lithium compound, eg. n-butyllithium, or an alkali metal hydride, eg. sodium hydride.

Instead of carrying out the reaction in the presence of an acid acceptor, it is also possible first to prepare a salt, for example an alkali metal salt, alkaline earth metal salt or ammonium salt, of the α-oximinonitrile of the formula II and then to react this salt further with the compound of the formula III.

The starting materials are conventionally employed in equimolar amounts, but an excess of one or other of the reactants may be advantageous in some cases.

The reaction temperature can be varied within a substantial range, and is in general from 0° to 120° C., preferably from 20° to 50° C. Where the reaction is exothermic, it can be advantageous to cool externally at the beginning of the reaction.

The reaction is conventionally carried out under atmospheric pressure.

The oximes of the formula II which are used as starting materials for the preparation of the compounds of the formula I have not been disclosed, but may be prepared in a conventional manner (German Published Application DAS No. 1,567,142), by chlorinating the corresponding isobutyraldoxime of the formula IV and reacting the product with sodium cyanide or potassium cyanide, in accordance with the following equation:

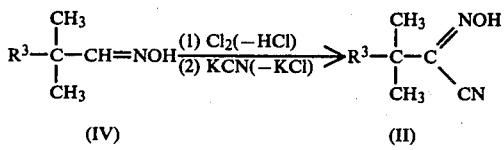

(IV)  →  (II)

Oximes of the formula IV where R³ is alkoxy are obtained by the process described in U.S. Pat. No. 2,496,198. The oxime in which R³ is methoxymethyl is obtained by reacting methoxypivalaldehyde (V) with hydroxylamine hydrochloride, in accordance with the following equation:

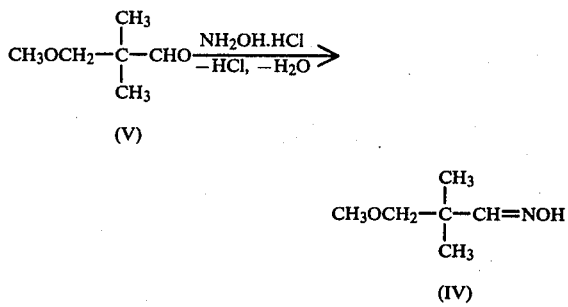

The (thiono)(thio)phosphoric(phosphonic) acid ester (amide) halides III additionally required for the synthesis of the compounds of the formula I have been disclosed in Houben-Weyl, Methoden der organischen Chemie, Volume XII/2 (1964), page 274 et seq., Georg Thieme-Verlag, Stuttgart, and may be prepared by the routes described in that publication.

Some of the oximinophosphoric acid derivatives of the formula I are obtained in the form of colorless or slightly brownish oils, which can be freed from the last volatile constituents by prolonged heating to moderately elevated temperatures under reduced pressure (incipient distillation), and purified in this manner. Compounds of the formula I which are obtained in crystalline form may be purified by recrystallization.

The oximinophosphoric acid derivatives of the formula I can occur in the isomeric syn and anti forms, and their melting or boiling ranges are therefore not very suitable for characterizing them; H-NMR spectra and elementary analyses are therefore used below for this purpose.

The Examples which follow illustrate the preparation of the oximinophosphoric acid derivatives of the formula I.

EXAMPLE 1

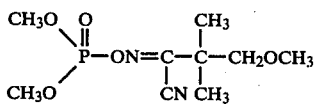

116 parts of methoxypivalaldehyde were dissolved in 600 parts of ethanol, and a solution of 76.5 parts of hydroxylamine hydrochloride and 86 parts of sodium acetate in 500 parts of water was added dropwise to the above, vigorously stirred solution, the temperature increasing temporarily to 40° C. Stirring was continued for 24 hours at room temperature, after which the mixture was poured into 4,000 parts of water and then saturated with sodium chloride and extracted with eight times 400 parts of ether. The combined extracts were dried over sodium sulfate, the solvent was stripped off, and the residue was distilled, giving 90.4 parts of methoxypivalaldoxime as a colourless liquid at 48°–49° C./0.1 mbar. Yield: 69% of theory.

$C_6H_{13}NO_2$ (131) Calculated: C, 54.9; H, 10.0; N, 10.7. Found: C, 54.8; H, 10.0; N, 10.9.

H-NMR spectrum, 60 MHz, in $CDCl_3$ (δ values): 1.15 (6H), 3.25 (2H), 3.35 (3H), 7.45 (1H), 7.8–9.2 (1H).

46.9 parts of chlorine gas were passed into a well-cooled solution of 78.5 parts of methoxypivalaldoxime in 800 parts of ether at below −20° C. Thereafter, all volatile constituents of the reaction mixture were stripped off at 20° C. in a rotary evaporator, the residue was taken up in 400 parts of ether, and the dark blue solution obtained was kept at room temperature until the chloronitroso compound formed had disappeared. The liquid, which was then colorless, was thereafter introduced, in the course of two hours, into a suspension of 42.9 parts of potassium cyanide in 450 parts of methanol, which had been cooled to 10°–15° C. The mixture was stirred for a further three hours at room temperature, the precipitated potassium chloride was filtered off under suction, the filtrate was concentrated, the residue was taken up in ether, washed three times with water and dried over magnesium sulfate, and the solvent was stripped off, in the final stage at 40° C./0.001 mbar, giving 75.1 parts of cyano-α-(2-methoxymethylprop-2-yl)-acetoxime in the form of a viscous oil which crystallizes completely after a short time. Melting point: 75°–76° C.; yield: 81% of theory.

$C_7H_{12}N_2O_2$ (156) Calculated: C, 53.8; H, 7.7; N, 17.9. Found: C, 54.2; H, 7.7; N, 18.0.

H-NMR spectrum, 60 MHz, in $CDCl_3$ (δ values): 1.30 (6H), 3.45 (5H), 12.1–12.8 (1H).

7.80 parts of α-oximino-(2-methoxymethylprop-2-yl)-acetonitrile and 7.41 parts of O,O-dimethylphosphoryl chloride in 60 parts of acetonitrile were initially taken, and 6.90 parts of finely powdered potassium carbonate were added to the thoroughly stirred mixture in the course of one and a half hours. The reaction mixture was stirred for 36 hours at room temperature and then filtered off under suction from insoluble material, the filtrate was concentrated under reduced pressure, the residue was taken up in ether, washed three times with water, dried over sodium sulfate and freed from solvent. Incipient distillation of the residue gave 12.2 parts of O-(O,O-dimethylphosphoryl)α-cyano-α-(2-methoxymethylprop-2-yl)-acetoxime as a colorless, viscous oil, at 50° C./0.02 mbar. Yield: 92% of theory.

$C_9H_{17}N_2O_5P$ (264) Calculated: C, 40.9; H, 6.5; N, 10.6. Found: C, 41.4; H, 6.7; N, 10.8.

H-NMR spectrum, 60 MHz, in $CDCl_3$ (δ values): 1.35 (6H), 3.45 (3H), 3.50 (2H), 3.95 (6H).

EXAMPLE 2

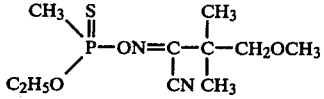

8.12 parts of O-ethyl-methylthiophosphonyl chloride were added dropwise to a solution of 7.80 parts of cyano-α-(2-methoxymethylprop-2-yl)-acetoxime in 60 parts of acetonitrile, and 6.90 parts of potassium carbonate were added a little at a time, while stirring thoroughly. After the addition was complete, the reaction mixture was kept at 30° C. for a further 12 hours. It was worked up by filtering off the potassium chloride formed, concentrating the filtrate, taking up the residue in ethyl acetate, washing the solution several times with water and drying it over sodium sulfate, and then removing the solvent, in the final stage at 35° C./0.02 mbar. 13.2 parts of O-(O-ethyl-methylthiophosphonyl)-α-cyano-α-(2-methoxymethylprop-2-yl)-acetoxime were obtained. Yield: 95% of theory.

$C_{10}H_{19}N_2O_3PS$ (278) Calculated: C, 43.2; H, 6.9; N, 10.1. Found: C, 43.3; H, 7.2; N, 10.4.

H-NMR spectrum, 220 MHz, in CDCl$_3$ (δ values): 1.25 (6H), 1.30 (3H), 1.97 (3H), 3.34 (3H), 3.40 (2H), 4.0–4.6 (2H).

EXAMPLE 3

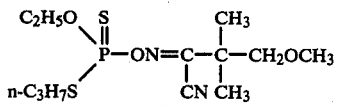

Using a procedure similar to that described in Example 1, 7.8 parts of α-cyano-α-(2-methoxymethylprop-2-yl)-acetoxime were reacted with 10.9 parts of O-ethyl-S-n-propyldithiophosphoryl chloride in the presence of 6.90 parts of potassium carbonate to give 15.7 parts of O-(O-ethyl-S-n-propyldithiophosphoryl)-α-cyano-α-(2-methoxymethylprop-2-yl)-acetoxime as a pale yellow oil. Yield: 92% of theory.

$C_{12}H_{23}N_2O_3PS_2$ (338) Calculated: C, 42.6; H, 6.9; N, 8.3. Found: C, 43.1; H, 7.1; N, 8.3.

H-NMR spectrum, 60 MHz, in CDCl$_3$ (δ values): 1.05 (3H), 1.35 (6H), 1.40 (3H), 1.60–2.20 (2H), 2.70–3.20 (2H), 3.40 (3), 3.45 (2H), 4.10–4.75 (2H).

EXAMPLE 4

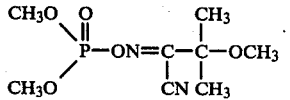

Using a procedure similar to that described in Example 1, 55.3 parts of α-cyano-α-(2-methoxyprop-2-yl)-acetoxime were obtained from 58.4 parts of 2-methoxyisobutyraldoxime, 38.9 parts of chlorine and 35.6 parts of potassium cyanide. Yield: 78% of theory.

$C_6H_{10}N_2O_2$ Calculated: C, 50.7; H, 7.1; N, 19.7. Found: C, 50.9; H, 7.0; N, 19.9.

H-NMR spectrum, 60 MHz, in CDCl$_3$ (δ values): 1.50 (6H), 3.20 (3H), 12.5–13.5 (1H).

7.10 parts of α-cyano-α-(2-methoxyprop-2-yl)-acetoxime, 6.90 parts of potassium carbonate and 7.40 parts of O,O-dimethylphosphoryl chloride were reacted as described in Example 1 to give 9.81 parts of O-(O,O-dimethylphosphoryl)-α-cyano-α-(2-methoxyprop-2-yl)-acetoxime as a virtually colorless, viscous oil. Yield: 78% of theory.

$C_8H_{15}N_2O_5P$ (250) Calculated: C, 38.4; H, 6.0; N, 11.2. Found: C, 38.9; H, 6.0; N, 11.3.

H-NMR spectrum, 80 MHz, in CDCl$_3$ (δ values): 1.50 (6H), 3.24 (3H), 3.87 (6H).

EXAMPLE 5

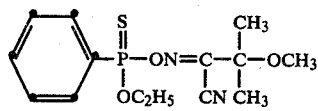

9.08 parts of O-ethylbenzenethiophosphonyl chloride were added dropwise to a solution of 5.86 parts of α-cyano-α-(2-methoxyprop-2-yl)-acetoxime in 60 parts of acetone, and 5.72 parts of potassium carbonate were added a little at a time, while stirring thoroughly. After the addition was complete, the reaction mixture was kept at 35° C. for a further 8 hours. It was worked up by filtering off the potassium chloride formed, concentrating the filtrate, taking up the residue in ethyl acetate, washing the solution thoroughly with water and drying it over sodium sulfate, and removing the solvent, in the final stage at 40° C./0.01 mbar. 12.83 parts of O-(O-ethylbenzenethiophosphonyl)-α-cyano-α-(2-methoxyprop-2-yl)-acetoxime were obtained as a pale yellow oil. Yield: 89% of theory.

$C_{14}H_{19}N_2O_3PS$ (350) Calculated: C, 51.5; H, 5.9. Found: C, 51.1; H, 5.9.

H-NMR spectrum, 80 MHz, in CDCl$_3$ (δ values): 1.42 (3H), 1.44 (6H), 3.08 (3H), 4.05–4.65 (2H), 7.25–7.7 (3H), 7.75–8.2 (2H).

EXAMPLE 6

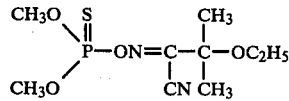

A solution of 52.4 parts of ethoxyisobutyraldoxime in 590 parts of ether was cooled to −30° C., 31.2 parts of chlorine were passed in at this temperature, and after the addition was complete the mixture was kept at −15° C. for a further 20 minutes. It was then concentrated under reduced pressure at 20° C., the partially crystalline residue was taken up in 320 parts of methylene chloride, and the solution was kept overnight at room temperature. This solution was added dropwise in the course of 1.5 hours to a thoroughly stirred suspension of 29.25 parts of potassium cyanide in 300 parts of methanol, which has been cooled to 15° C. After 3 hours, the precipitated potassium chloride was filtered off under suction, the liquid phase was concentrated, the residue was taken up in 400 parts of ether, the solution was washed three times with water and dried over sodium sulfate, and the solvent was removed completely under 0.02 mbar. 49.4 parts of a crystalline solid of melting point 77°–78° C. were obtained. Yield: 79% of theory.

$C_7H_{12}N_2O_2$ (156) Calculated: C, 53.8; H, 7.7; N, 17.9. Found: C, 54.1; H, 7.8; N, 18.3.

H-NMR spectrum, 60 MHz, in CDCl$_3$ (δ values): 1.25 (3H), 1.50 (6H), 3.40 (2H), 9.4–10.3 (1H).

6.62 parts of potassium carbonate are added continuously to a solution of 7.48 parts of α-cyano-α-(2-ethoxyprop-2-yl)-acetoxime and 7.89 parts of O,O-dimethylthiophosphoryl chloride in 60 parts of methyl ethyl ketone, the temperature increasing temporarily to 28° C. The mixture was stirred for 24 hours at 20° C. and then filtered off under suction from the potassium chloride formed, the filtrate was freed from the solvent under reduced pressure, the residue was taken up in 200 parts of ethyl acetate, washed three times with water, dried over sodium sulfate and concentrated, and the solvent was stripped off at 30° C./0.02 mbar. 11.1 parts of O-(O,O-dimethylthiophosphoryl)-α-cyano-α-(2-ethoxyprop-2-yl)-acetoxime were obtained. Yield: 82% of theory.

$C_9H_{17}N_2O_4PS$ (280) Calculated: C, 38.6; H, 6.1; N, 10.0. Found: C, 38.8; H, 6.1; N, 10.1.

H-NMR spectrum, 60 MHz, in $CDCl_3$ (δ values): 12.5 (3H), 1.50 (6H), 3.45 (2H), 3.90 (6H).

EXAMPLE 7

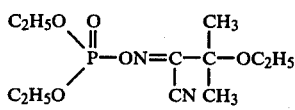

Using a procedure similar to that described in Example 6, 12.6 parts of O-(O,O-diethylthiophosphoryl)-α-cyano-α-(2-ethoxyprop-2-yl)-acetoxime were obtained as a yellowish oil by reacting 7.48 parts of α-cyano-α-(2-ethoxyprop-2-yl)-acetoxime with 8.27 parts of O,O-diethylphosphoryl chloride and 6.62 parts of potassium carbonate in 60 parts of acetonitrile. Yield: 90% of theory.

$C_{11}H_{21}N_2O_5P$ (292) Calculated: C, 45.2; H, 7.2; N, 9.6. Found: C, 44.8; H, 7.4; N, 9.5.

H-NMR spectrum, 360 MHz, in $CDCl_3$ (δ values): 1.22 (3H), 1.40 (6H), 1.51 (6H), 3.40 (2H), 4.25 (4H).

EXAMPLE 8

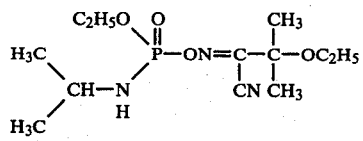

13.60 parts of O-(O-ethyl-N-isopropylamidophosphoryl)-α-cyano-α-(2-ethoxyprop-2-yl)-acetoxime were obtained by reacting 7.80 parts of α-cyano-α-(2-ethoxyprop-2-yl)-acetoxime with 9.28 parts of O-ethyl-N-isopropylamidophosphoryl chloride in the presence of 6.90 parts of potassium carbonate and 50 parts of acetonitrile. Yield: 89% of theory.

$C_{12}H_{24}N_3O_4P$ (305): Calculated: C, 47.2; H, 7.9; N, 13.7. Found: C, 47.6; H, 7.8; N, 13.6.

H-NMR spectrum, 60 MHz, in $CDCl_3$ (δ values): 12.5 (6H), 1.30 (3H), 1.55 (6H), 3.05–3.35 (1H), 3.45 (2H), 4.30 (2H).

EXAMPLE 9

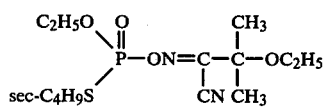

7.80 parts of α-cyano-α-(2-ethoxyprop-2-yl)-acetoxime were dissolved in 50 parts of absolute tetrahydrofuran, and the solution was added dropwise to a stirred suspension of 1.57 parts of sodium hydride (20% strength in paraffin oil) in 10 parts of tetrahydrofuran. Stirring was continued at room temperature until the evolution of hydrogen had ended, about 4 hours being required, and 10.1 parts of O-ethyl-S-but-2-ylthiophosphoryl chloride were then added. After 24 hours, the solvent was stripped off under reduced pressure, the residue was taken up in 200 parts of a 3:1 pentane/ether mixture, the solution was washed three times with water and dried over sodium sulfate, and the solvent was removed. 13.4 parts of O-(O-ethyl-S-but-2-ylthiophosphoryl)-α-cyano-α-(2-ethoxyprop-2-yl)-acetoxime were obtained. Yield: 83% of theory.

$C_{13}H_{25}N_2O_4PS$ (322) Calculated: C, 44.7; H, 7.2; N, 8.7. Found: C, 45.1; H, 7.0; N, 8.6.

H-NMR spectrum, 80 MHz, in $CDCl_3$ (δ values): 1.00 (3H), 1.20 (3H), 1.35 (3H), 1.40 (3H), 1.50 (6H), 3.15–3.65 (3H), 4.05–4.50 (2H).

The following compounds of the formula I for example, were prepared in a similar manner:

| No. | $R^1$ | $R^2$ | $R^3$ | X | H—NMR data (MHz, solvent, δ values) |
|---|---|---|---|---|---|
| 10 | $CH_3$ | $C_2H_5$ | $CH_2OCH_3$ | S | (60, $CDCl_3$) 1.20 (3H), 1.35 (6H), 21.14 (2H), 3.30 (3H), 3.35 (2H), 3.75 (3H) |
| 11 | $CH_3$ | $OCH_3$ | $CH_2OCH_3$ | S | (60, $CDCl_3$) 1.37 (6H), 3.41 (3H), 3.48 (2H), 3.82 (2H), 3.95 (6H) |
| 12 | $C_2H_5$ | $OC_2H_5$ | $CH_2OCH_3$ | S | (60, $CDCl_3$) 1.35 (6H), 1.44 (6H), 3.40 (3H), 3.45 (2H), 4.10–4.75 (4H) |
| 13 | $C_2H_5$ | $C_2H_5$ | $CH_2OCH_3$ | S | (60, $CDCl_3$) 1.35 (6H), 1.37 (3H), 2.21 (2H), 3.38 (3H), 3.43 (2H), 4.03–4.65 (2H) |
| 14 | $C_2H_5$ | $OC_2H_5$ | $CH_2OCH_3$ | O | (60, $CDCl_3$) 1.35 (6H), 1.40 (6H), 3.40 (3H), 3.45 (2H), 4.10–4.65 (4H) |
| 15 | $C_2H_5$ | $C_6H_5$ | $CH_2OCH_3$ | S | (60, $CDCl_3$) 1.35 (6H), 1.55 (3H), 3.40 (3H), 3.45 (2H), 4.2–4.85 (2H), 7.50–7.95 (3H), 8.00–8.50 (2H) |
| 16 | $C_2H_5$ | $OC_2H_5$ | $OCH_3$ | S | (100, $CCl_4$) 1.40 (6H) 1.52 (6H), 3.23 (3H), 4.10–4.48 (4H) |
| 17 | $C_2H_5$ | $OC_2H_5$ | $OCH_3$ | O | (100, $CCl_4$) 1.38 (6H), 1.50 (6H), 3.21 (3H), 4.10–4.47 (4H) |
| 18 | $C_2H_5$ | $S—n-C_3H_7$ | $OC_2H_5$ | S | (360, $CDCl_3$) 1.05 (3H), 1.20 (3H), 1.42 (3H), 1.53 (6H), 1.75 (2H), 2.98 (2H), 3.36 (2H), 4.28 (2H) |
| 19 | $C_2H_5$ | $C_2H_5$ | $OCH_3$ | S | (360, $CCl_4$) 1.22 (3H), 1.33 (3H), 1.52 (6H), 2.18 (2H), 3.23 (3H), 4.26 (2H) |
| 20 | $C_2H_5$ | $S—n-C_3H_7$ | $OCH_3$ | S | (360, $CDCl_3$) 1.02 (3H), 1.40 (3H), 1.52 (6H), 1.75 (2H), 2.98 (2H), 3.23 (3H), 4.30 (2H) |
| 21 | $CH_3$ | $OCH_3$ | $OC_2H_5$ | O | (60, $CDCl_3$) 1.35 (3H), 1.40 (6H), 3.55 (2H), 3.95 (6H) |
| 22 | $C_2H_5$ | $OC_2H_5$ | $OC_2H_5$ | S | (60, $CDCl_3$) 1.37 (3H), 1.50 (6H), 1.60 (6H), 3.55 (2H), 4.10–4.75 (4H) |
| 23 | $CH_3$ | $C_2H_5$ | $OCH_3$ | S | (60, $CDCl_3$) 1.30 (3H), 1.55 (6H), 2.15 |

-continued

| No. | R$^1$ | R$^2$ | R$^3$ | X | H—NMR data (MHz, solvent, δ values) |
|---|---|---|---|---|---|
| 24 | CH$_3$ | OCH$_3$ | OCH$_3$ | O | (2H), 3.20 (3H), 3.80 (3H)<br>(80, CDCl$_3$) 1.50 (6H), 3.25 (3H), 3.95 (6H) |
| 25 | C$_2$H$_5$ | C$_2$H$_5$ | OC$_2$H$_5$ | S | (60, CDCl$_3$) 1.30 (3H), 1.34 (3H), 1.45 (3H), 1.60 (6H), 2.20 (2H), 3.55 (2H), 4.10–4.70 (2H) |
| 26 | CH$_3$ | C$_2$H$_5$ | OC$_2$H$_5$ | S | (60, CDCl$_3$) 1.25 (3H), 1.30 (3H), 1.50 (6H), 2.25 (2H), 3.50 (2H), 3.90 (3H) |
| 27 | C$_2$H$_5$ | S—n-C$_3$H$_7$ | OC$_2$H$_5$ | O | (60, CDCl$_3$) 1.10 (3H), 1.35 (3H), 1.45 (3H), 1.55 (6H), 1.80 (2H), 3.00 (2H), 3.45 (2H), 4.00–4.70 (2H) |
| 28 | C$_2$H$_5$ | CH$_3$ | OC$_2$H$_5$ | S | (60, CDCl$_3$) 1.30 (3H), 1.40 (3H), 1.60 (6H), 2.05 (3H), 3.45 (2H), 4.25 (2H) |
| 29 | C$_2$H$_5$ | N(CH$_3$)$_2$ | OC$_2$H$_5$ | O | (60, CDCl$_3$) 1.35 (3H), 1.50 (3H), 1.65 (6H), 2.85 (6H), 3.50 (2H), 4.00–4.60 (2H) |
| 30 | C$_2$H$_5$ | S—sec.-C$_4$H$_9$ | OC$_2$H$_5$ | S | (80, CCl$_4$) 1.05 (3H), 1.20 (3H), 1.35 (3H), 1.40 (3H), 1.50 (6H), 1.65 (2H), 3.20–3.65 (3H), 4.05–4.50 (2H) |
| 31 | C$_2$H$_5$ | S—sec.-C$_4$H$_9$ | OCH$_3$ | S | (360, CDCl$_3$) 1.03 (3H), 1.44 (3H), 1.47 (3H), 1.51 (6H), 3.24 (3H), 3.47 (1H), 4.30 (2H) |
| 32 | C$_2$H$_5$ | NH(CH$_3$)$_2$ | OC$_2$H$_5$ | S | (60, CDCl$_3$) 1.25 (6H), 1.30 (3H), 1.60 (6H), 3.05–3.35 (1H), 3.43 (2H), 4.35 (2H) |
| 33 | C$_2$H$_5$ | N(CH$_3$)$_2$ | OC$_2$H$_5$ | S | (60, CDCl$_3$) 1.35 (3H), 1.50 (3H), 1.60 (6H), 2.85 (6H), 3.50 (2H), 4.05–4.65 (2H) |
| 34 | C$_2$H$_5$ | S—iso-C$_4$H$_9$ | OC$_2$H$_5$ | O | (60, CDCl$_3$) 1.05 (6H), 1.25 (3H), 1.40 (3H), 1.55 (6H), 1.95 (1H), 2.85 (2H), 3.60 (2H), 4.00–4.60 (2H) |
| 35 | C$_2$H$_5$ | SCH$_2$CH$_2$OCH(CH$_3$)$_2$ | OC$_2$H$_5$ | O | (60, CDCl$_3$) 1.15 (6H), 1.25 (3H), 1.45 (3H), 1.55 (6H), 2.75–3.35 (2H), 3.40–3.65 (5H), 4.00–4.55 (2H) |
| 36 | C$_2$H$_5$ | SCH$_2$CH$_2$OCH$_3$ | OC$_2$H$_5$ | O | (60, CDCl$_3$) 1.25 (3H), 1.50 (3H), 1.60 (6H), 3.05 (2H), 3.30 (3H), 3.50 (2H), 3.60 (2H), 4.05–4.65 (2H) |

The oximinophosphoric acid derivatives of the formula I according to the invention are suitable for effectively combating pests from the classes of insects, mites, ticks, and nematodes.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarius, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymantria dispar., Lymantria monacha, Pieris brassicae, Aporia crataegi,* and *Heliothis virescens;* examples from the Coleoptera order are *Blitophaga undata, Melanotus communis, Limonius californicus, Agriotes lineatus, Agricotes obscurus, Agrilus sinuatus, Meligethes aeneus, Atomaria linearis, Epilachna varivestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Lycoria pectoralis, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Musca domestica, Fannia canicularis, Muscina stabulans, Glossina morsitans, Oestrus ovis, Chrysomya macellaria, Chrysomya hominivorax, Lucilia cuprina, Lucilia sericata,* and *Hypoderma lineata;* examples from the Hymenoptera order are *Athalia rosae, Hoplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysaphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* examples from the Isoptera order are *Reticulitermes lucifugus, Calotermes flavicollis, Leucotermes flavipes,* and *Termes natalensis;*

Examples from the Orthoptera order are *Forficula auricularia, Acheta domestica, Gryllotalpa gryllotalpa, Tachycines asynamorus, Locusta migratoria, Stauronotus maroccanus, Schistocerca peregrina, Nomadacris septem-*

*fasciata, Melanoplus spretus, Melanoplus femur-rubrum, Blatta orientalis, Blattella germanica, Periplaneta americana,* and *Blabera gigantea.*

Examples of mites and ticks (Acarina) belonging to the Arachnida class are *Tetranychus telarius, Tetranychus atlanticus, Tetranychus pacificus, Paratetranychus pilosus, Bryobia praetiosa, Ixodes ricinus, Ornithodorus moubata, Ablyomma americanum, Dermacentor silvarum,* and *Boophilus microplus.*

Examples from the Nemathelminthes class are root-knot nematodes, e.g., *Meloidogyne incognita, Meloidogyne hapla,* and *Meloidogyne javanica,* cyst-forming nematodes, e.g., *Heterodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratylenchus penetrans, Pratylenchus goodeyi, Pratylenchus curvitatus* and *Tylenchorhynchus dubius, Tylenchorhynchus claytoni, Rotylenchus robustus, Heliocotylenchus multicinctus, Radopholus similis, Belonolaimus longicaudatus, Longidorus elongatus,* and *Trichodorus primitivus.*

The compounds according to the invention may be successfully employed as pesticides in crop protection, and in the hygiene, stores protection and veterinary sector.

The active ingredients may be applied as such, as formulations, or ready-to-use application forms prepared therefrom, e.g., as directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Examples of formulations are given below.

I. 3 parts by weight of compound 1 is intimately mixed with 97 parts by weight of particulate kaolin. A dust is obtained containing 3% by weight of the active ingredient.

II. 30 parts by weight of compound 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 20 parts by weight of compound 7 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

IV. 20 parts by weight of compound 6 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably from 0.5 to 90, wt% of active ingredient.

The amount of active ingredient in the ready-to-use formulations may vary within a wide range; it is generally from 0.0001 to 10%, preferably from 0.01 to 1%.

The active ingredients may also be successfully used in the ultra-low volume method, where it is possible to apply formulations containing more than 95% of active ingredient, or even the 100% active ingredient.

There may be added to the individual active ingredients (if desired, immediately before use (tankmix)) oils of various types, herbicides, fungicides, other insecticides and bactericides. These agents may be added to the active ingredients according to the invention in a weight ratio of from 1:10 to 10:1.

Examples of active ingredients which may be admixed are as follows:

1,2-dibromo-3-chloropropane, 1,3-dichloropropene, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-B 4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenylphosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, alpha-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl(±)-cis,trans-2,2-dimethyl-3-(2,2-dichlorovinyl)-cyclopropanecarboxylate, alpha-cyano-3-phenoxybenzyl(±)-cis,trans-2,2-dimethyl-3-(2,2-dichlorovinyl)-cyclopropane carboxylate, (s)-alpha-cyano-3-phenoxybenzyl-cis(1R,3R)-2,2-dimethyl-3-(2,2-dibromovinyl)-cyclopropane carboxylate, 3,4,5,6-tetrahydrophthalimidoethyl-DL-cis,trans-chrysanthemate, 2-methyl-5-(2-propynyl)-3-furylmethyl-chrysanthemate, and alpha-cyano-3-phenoxybenzyl-alpha-isopropyl-4-chlorophenylacetate.

The following examples demonstrate the biological action of the novel compounds. Oximinophosphoric acid derivatives disclosed in German Printed Application DE-AS Nos. 1,052,981 and DE-AS 2,243,370 were used as comparative agents.

The active ingredients according to the invention are numbered as in the examples and the tables.

EXAMPLE A

Contact Action on Oriental Cockroaches (*Blatta orientalis*)

The bottoms of 1 liter preserving jars was lined with acetonic solutions of the active ingredients. After the solvent had evaporated, 5 adult cockroaches were introduced into each jar. The kill rate was determined after 48 hours.

In this test, active ingredients nos. 2, 3, 6, 7, 9, 10, 11, 13, 16, 17, 18, 19, 20, 21, 22, 23, 24, 25, 26 and 27 had a better action than the comparative agents.

EXAMPLE B

Contact Action on Houseflies (*Musca domestica*)

1 μl of the active ingredient dissolved in acetone was administered, by means of a microsyringe, to the ventral abdomen of 4-day old imagoes under slight $CO_2$ narcosis. 20 animals treated in the same way were then placed in a plastic bag having a volume of approximately 500 ml.

After 4 hours the animals in supine position were counted, and the $LD_{50}$ was worked out.

In this test, active ingredients nos. 1, 2, 6, 7, 10, 11, 12, 13, 19, 21, 22, 23, 24 and 25 had a superior action.

EXAMPLE C

Contact Action on Bean Aphids (*Aphis fabae*), Spray Experiment

Potton bean plants (*Vicia faba*) with extensive bean aphid colonies were sprayed to runoff in a spray booth with aqueous formulations of the active ingredients. Assessment took place after 48 hours.

In this test, active ingredients nos. 1, 2, 4, 5, 6, 7, 13, 14, 16, 17, 19, 20, 21, 22, 23, 24, 25, 25, 27, 30 and 31 had a superior action.

EXAMPLE D

Contact Action on Ticks (*Ornithodorus moubata*)

Ticks in the 3rd larval stage were placed in paper bags and dipped for 3 seconds in the candidate emulsions. The bags were then suspended. The action on the ticks was assessed after 48 hours.

In this test, active ingredients nos. 1, 4, 5, 8, 10, 11, 13, 14, 16, 17, 19, 21, 22, 23, 24, 25, 26, 28 and 29 had a superior action.

EXAMPLE E

Action on Root-Knot Nematodes (*Meloidogyne incognita*)

20 ml of aqueous formulations of the active ingredients was poured on to 500 g of mold heavily infested with *Meloidogyne incognita*.

The roots were checked for root-knots after 6 to 8 weeks.

In this test, active ingredients nos. 1, 3, 9, 11, 15 and 18 were superior to prior art active ingredients of similar structure.

EXAMPLE F

Continuous Contact Action on Houseflies (*Musca domestica*)

Both covers and bottoms of Petri dishes 10 cm in diameter were lined with a total per dish of 2 ml of acetonic solutions of the active ingredients. After the solvent has evaporated (about 30 min.), 20 4-day old flies were introduced into each dish.

In this test, active ingredients nos. 1, 2, 4, 7, 10, 11, 13, 14, 16, 17, 19, 21, 23, 24, 28 and 30 achieved a very high kill rate.

EXAMPLE G

Contact Action and Effect of Ingested Food on Caterpillars of the Diamondback Moth (*Plutella maculipennis*)

Leaves of young cabbage plants were dipped for 3 seconds in aqueous emulsions of the active ingredients, and, after briefly having allowed excess liquid to drip off, were placed on a moist filter paper in a Petri dish. 10 caterpillars of the 4th stage were then placed on the leaves. The action was assessed after 48 hours.

In this test, for example active ingredients nos. 2, 4, 5, 6, 7, 10, 11, 13, 16, 17, 19, 20, 22, 23, 24, 25, 26, 27, 30 and 31 had a better action than the prior art compounds.

We claim:

1. An oximinophosphoric acid derivative of the formula

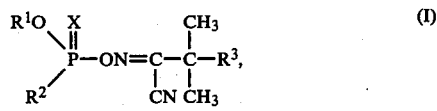

where $R^1$ is straight-chain or branched alkyl of not more than 4 carbon atoms, $R^2$ is a straight-chain or branched alkoxy or alkylthio group of not more than 4 carbon atoms, straight-chain or branched alkoxyalkylthio of not more than 6 carbon atoms, straight-chain or branched alkyl of not more than 3 carbon atoms, phenyl or a straight-chain or branched alkylamino or dialkylamino radical where each alkyl is of not more than 4 carbon atoms, $R^3$ is straight-chain or branched alkoxy of not more than 4 carbon atoms or methoxymethyl, and X is oxygen or sulfur.

2. O-(O,O-diethylthiophosphoryl)-alpha-cyano-alpha-(2-ethoxy-prop-2-yl)-acetoxime.

3. O-(O,O-dimethylthiophosphoryl)-alpha-cyano-alpha-(2-ethoxy-prop-2-yl)-acetoxime.

4. A pesticide containing a solid or liquid carrier and at least one oximinophosphoric acid derivative of the formula I as claimed in claim 1.

5. A process for combating pests, wherein an effective amount of an oximinophosphoric acid derivative of the formula I as claimed in claim 1 is allowed to act on the pests or their habitat.

* * * * *